United States Patent [19]

Mitsukuchi et al.

[11] Patent Number: 4,968,822
[45] Date of Patent: Nov. 6, 1990

[54] 21-ALKOXYSTEROID COMPOUNDS

[75] Inventors: Morihiro Mitsukuchi; Tomoyuki Ikemoto; Minoru Taguchi; Katsuo Hatayama, all of Omiya; Kaoru Sota, Tokorozawa, all of Japan

[73] Assignee: Taisho Pharmaceutical Co., Ltd., Japan

[21] Appl. No.: 279,454

[22] Filed: Dec. 5, 1988

[30] Foreign Application Priority Data

Dec. 11, 1987 [JP] Japan ................................ 62-313879

[51] Int. Cl.$^5$ ............................................. C07J 1/00
[52] U.S. Cl. ................................................... 552/574
[58] Field of Search ...................... 260/397.45; 552/574

[56] References Cited

U.S. PATENT DOCUMENTS

| | | | |
|---|---|---|---|
| 4,588,530 | 5/1986 | Lee | 260/397.45 |
| 4,619,922 | 10/1986 | Annen et al. | 260/397.45 |
| 4,645,763 | 2/1987 | Annen et al. | 260/397.45 |

FOREIGN PATENT DOCUMENTS

| | | |
|---|---|---|
| 108894 | 8/1980 | Japan . |
| 108895 | 8/1980 | Japan . |
| 108896 | 8/1980 | Japan . |
| 108897 | 8/1980 | Japan . |
| 108900 | 8/1980 | Japan . |

OTHER PUBLICATIONS

Chemical Abstracts; vol. 94 (1981), #103680-4; Patpharma Est.
Chemical Abstracts, col. 103, No. 7, Aug. 19, 1985, p. 607, Abstract No. 54360f.
The Journal of Organic Chemistry, vol. 32, No. 4, Apr. 12, 1987, pp. 1264-1265, "Diazomethane-Fluoroboric Acid Treatment of Some Corticoids".

Primary Examiner—Joseph A. Lipovsky
Attorney, Agent, or Firm—Lorusso & Loud

[57] ABSTRACT

A 21-alkoxysteroid compound represented by the formula

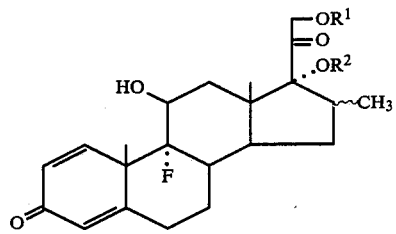

wherein $R^1$ is an alkyl group having 1 to 4 carbon atoms or a methylthiomethyl group, $R^2$ is an alkanoyl group having 2 to 7 carbon atoms, and a wavy line indicates the α- or β-configuration has anti-inflammatory activity.

3 Claims, No Drawings

21-ALKOXYSTEROID COMPOUNDS

BACKGROUND OF THE INVENTION (1) Field of the Invention

The present invention relates to 21-alkoxysteroid compounds having excellent anti-inflammatory effect.

(2) Prior Art

Corticosteroid 21-alkoxy-17-ester derivatives, while being disclosed in Japanese Patent Kokai 60-4200, are few reported because of the difficulty on their preparation.

Various corticosteroids for prevention, therapy and treatment of inflammatory skin diseases, asthmatically allegic diseases and rheumatic diseases are commercially available as non-prescription drugs or prescription drugs. However, these commercially available corticosteroids for non-prescription drugs or prescription drugs do not have sufficient effect.

SUMMARY OF THE INVENTION

As a result of the various researches, the present inventors have successed in preparing 21-alkoxysteroid compounds having potent anti-inflammatory activity.

An object of the present invention is to provide 21-alkoxysteroid compounds represented by the formula

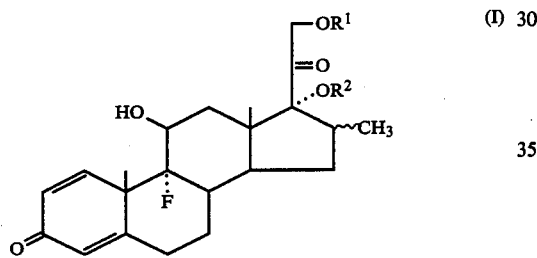

wherein $R^1$ is an alkyl group having 1 to 4 carbon atoms or a methylthiomethyl group, $R^2$ is an alkanoyl group having 2 to 7 carbon atoms, and a wavy line indicates the α- or β-configuration.

DETAILED DESCRIPTION OF THE INVENTION

In formula (I) of 21-alkoxysteroid compounds of the present invention, the alkyl group having 1 to 4 carbon atoms refers to a methyl group, an ethyl group, a propyl group and the like. The alkanoyl group having 2 to 7 carbon atoms refers to an alkanoyl group having a straight or branched chain alkyl group such as, for example, an acetyl group, a propionyl group, a butyryl group, an isobutyryl group, a valeryl group, an isovalery group and the like, preferably an alkanoyl group having 2 to 4 carbon atoms.

Among the preferred compounds of the present invention are compounds of Formula (I) wherein $R^2$ is an acetyl group, a propionyl group or a butyryl group.

The compounds of the present invention can be prepared, for example, by the following methods.

Compounds of Formula (I) wherein $R^1$ is an alkyl group having 1 to 4 carbon atoms can be prepared according to the following reaction scheme wherein $R^3$ is the alkyl group for $R^1$, X is a halogen atom and $R^2$ is as defined above.

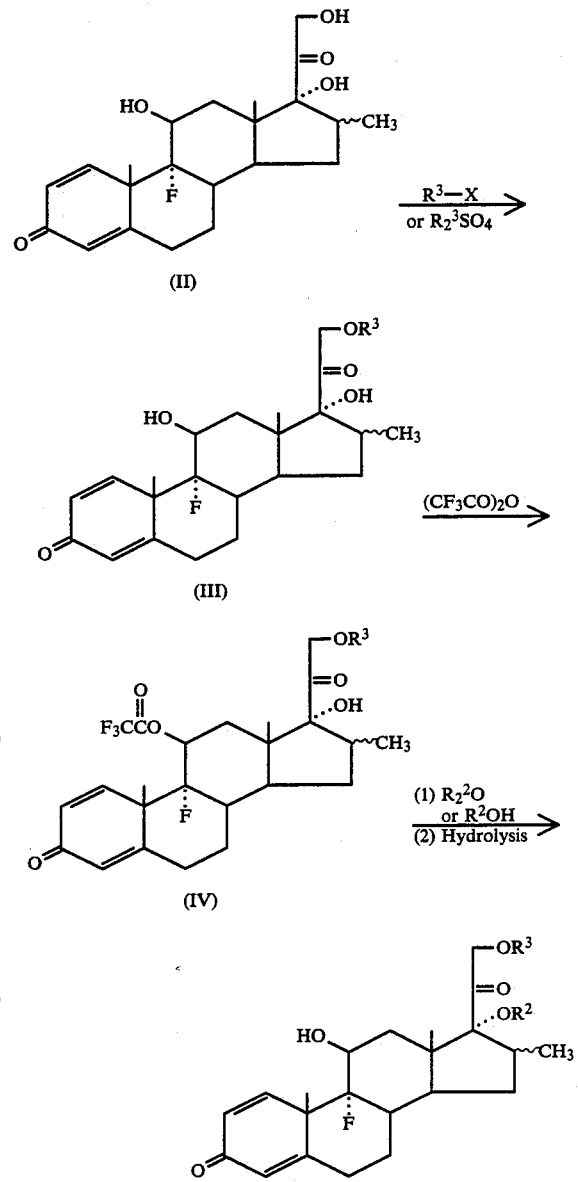

According to the reaction scheme, a known compound of Formula (II) is reacted with 1.0 to 10.0 equivalents of an alkyl halide of the formula $R^3$-X (wherein $R^3$ and X are as defined above) or with 1.0 to 10.0 equivalents of a dialkyl sulfate of the formula $R^3{}_2SO_4$ (wherein $R^3$ is as defined above) in the presence of 1.0 to 1.5 equivalents of a base to give a compound of Formula (III).

Examples of the base used in this reaction are alkali hydrides such as sodium hydride, potassium hydride and the like; alcoholates such as potassium tert-butoxide and the like; alkali hydroxides such as sodium hydroxide, potassium hydroxide and the like; alkali carbonates such as sodium carbonate, potassium carbonate and the like. Examples of the alkyl halide of the formula $R^3$-X are methyl iodide, ethyl iodide, propyl iodide and the like, and examples of the dialkyl sulfate of the formula $R^3{}_2SO_4$ are dimethyl sulfate and the like. The reaction can be carried out in a solvent such as ether system solvents (e.g., tetrahydrofuran, dioxane and the like), amide system solvents (e.g., N,N-dimethylformamide, dimethyl sulfoxide, hexamethylphosphortriamide and the like) or a mixture thereof with stirring at −30° C. −10° C. for 1 to 10 hours.

Then, the compound of Formula (III) obtained in the above is reacted with 1 to 10 equivalents of trifluoroacetic anhydride to give a compound of Formula (IV). This reaction can be also carried out in the presence of a base. Examples of the base are organic bases such as pyridine, triethylamine, diisopropylamine and the like. Furthermore, the reaction can be carried out in a solvent such as N,N-dimethylformamide, chloroform, dichloromethane, tetrahydrofuran, benzene and the like or without solvent at a reaction temperature of from −50° to 5° C. for a reaction time of from 5 minutes to 3 hours. Then, the hydroxy group at the 17-position of the compound of Formula (IV) obtained above is acylated followed by hydrolysis of the trifluoroacetate at the 11-position to give the compound of the present invention. The acylation used may be a reaction using a carboxylic anhydride of the formula $R^2_2O$ (wherein $R^2$ is as defined above) such as acetic anhydride, propionic anhydride, butyric anhydride and the like, without solvent or in an organic solvent (e.g., dichloromethane, benzene and the like) in the presence of an acid (e.g., p-toluenesulfonic acid, 60 to 70% perchloric acid and the like) or a reaction using a carboxylic acid of the formula $R^2$-OH (wherein $R^2$ is as defined above) such as acetic acid, propionic acid, butyric acid and the like, without solvent or in an organic solvent (e.g., dichloromethane, benzene and the like) in the presence of trifluoroacetic anhydride, an alkyl chloroformate and the like. Usually, these reactions may be carried out at room temperature and accomplished in 10 minutes to 5 days. The hydrolysis can be carried out by adding an organic solvent (e.g., N,N-dimethylformamide, tetrahydrofuran, methanol and the like) and an aqueous sodium acetate solution (or an aqueous sodium hydrogen-carbonate solution) to the above reaction solution, and stirring the mixture at 20° to 100° C. for 10 minutes t 3 hours.

On the other hand, a compound of Formula I wherein $R^1$ is a methylthiomethyl group can be obtained by the reaction of a known 21-hydroxysteroid compound of the formula

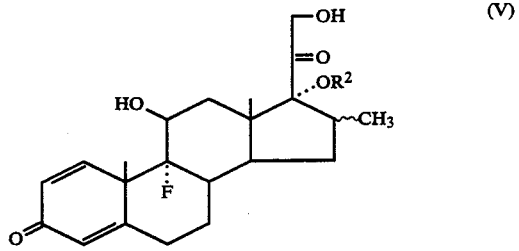

(V)

(wherein $R^2$ is as defined above) with dimethyl sulfoxide in the presence of a carboxylic anhydride and a carboxylic acid. Examples of the carboxylic anhydride are acetic anhydride, propionic anhydride and the like, and examples of the carboxylic acid are acetic acid, propionic acid and the like. This reaction may be carried out without solvent or in a nitrile system solvent (e.g., acetonitrile and the like) at a reaction temperature of from room temperature to 100° C. for a reaction time of from 10 minutes to 20 hours.

The compounds obtained by the above reactions can be separated from the reaction mixture and purified by the procedures known per se, for example, column chromatography, recrystallization and the like.

The compounds of Formula (I) of the present invention have excellent topical anti-inflammatory effect when compared with the closer compounds (e.g., betamethasone 21-methoxide, betamethasone 17-valerate and hydrocortisone 17-methylsuccinate 21-methoxide described in Japanese Patent Kokai No. 60-4200), therefore, the compounds of Formula (I) are useful for therapy of various clinical skin diseases such as, for example, acute eczema, chronic eczema, seborrheric eczema, atopic dermatitis, infantile eczema, contact dermatitis, psoriasis vulgaris and the like. Furthermore, these compounds can be used for prevention, therapy and treatment of diseases caused by inflammation such as asthmatic allergy diseases, rheumatic diseases and the like. For the purposes, the compounds of Formula (I) can be administered topically by conventional dosage forms (e.g., ointments, creams, lotions, solutions, plasters and the like), all of which can be prepared by ordinary practices. The amount of the compound of the present invention in the above dosage form may be in the range of 0.01 to 5.0% by weight.

EXPERIMENT 1 [VASOCONSTRICTION TEST]

Ointments containing each 0.01% (w/w) of the compounds of Formula (I) and the comparative drugs (betamethasone 21-methoxide, betamethasone 17-valerate and hydrocortisone 17-methylsuccinate 21-methoxide) were prepared using white petrolatum as a basal ingredient. Adhesive plasters for patch test (Finn chamber, manufactured by Epitest Ltd. Oy, Finland) painted with a given amount (20 mg) of the ointment each were applied to the bending sites of both forearms of twenty male adult volunteers. Four hours later, these adhesive plasters were removed, and the remaining drug on the skin was softly wiped off by a cotton impregnated with spirit. The degrees of the blanching were judged after 2 and 4 hours, and divided into four degrees, with + +indicating remarkable, +moderate, ± slight and −ineffective, which were scored as 3, 2, 1 and 0, respectively. The scores of twenty subjects were sumed, from which the average scores were calcurated (maximum point : 3.00).

The results are shown in Table 1. The compound numbers in Table 1 are as defined in the following Examples.

TABLE 1

| Compound No. | Degree of blanching (point) | |
|---|---|---|
| | 2 hours | 4 hours |
| 1 | 2.70 | 2.90 |
| 2 | 2.15 | 2.50 |
| 3 | 2.40 | 2.80 |
| 7 | 2.60 | 2.85 |
| 8 | 2.30 | 2.75 |
| 13 | 2.40 | 2.45 |
| 14 | 2.40 | 2.50 |
| 15 | 2.35 | 2.55 |
| 16 | 2.40 | 2.75 |
| 17 | 2.60 | 2.70 |
| 18 | 2.50 | 2.80 |
| A | 0.50 | 0.55 |
| B | 1.75 | 2.20 |
| C | 1.31 | 1.51 |

(Note) A: Betamethasone 21-methoxide
B: Betamethasone 17-valerate
C: Hydrocortisone 17-methylsuccinate 21-methoxide

EXPERIMENT 2 [DILUTION VASOCONSTRICTION TEST]

Ointments containing each 0.005% and 0.00125% (w/w) of betamethasone 17-propionate 21-methoxide of the present invention and betamethasone 17-valerate of a comparative drug were prepared using white petrolatum as as a basal ingredient. Following a procedure similar to that of Experiment 1 using these ointments, the blanching after 2 and 4 hours was measured.

Results are shown in Table 2.

TABLE 2

| Ointment concentration (w/w %) | Compound No. | Degree of blanching (point) 2 hours | 4 hours |
|---|---|---|---|
| 0.00125 | 1 | 2.40 | 2.55 |
|  | B | 1.25 | 1.45 |
| 0.005 | 1 | 2.50 | 2.65 |
|  | B | 1.80 | 1.95 |

(Note) B: Betamethasone 17-valerate

The present invention is illustrated by Examples in more detail.

EXAMPLE 1

(1) With 20 ml of n-hexane was washed 1.23 g of 60% oily sodium hydride under a nitrogen atmosphere, and 100 ml of tetrahydrofuran was added. To the mixture was added dropwise a mixture of 10 g of betamethasone, 30 ml of N,N-dimethylformamide and 20 ml of tetrahydrofuran under ice cooling, and after completion of the addition, the mixture was stirred at the same temperature for 10 minutes. Then, 5 ml of methyl iodide was added, and the mixture was stirred for a further 5 hours. After the reaction, ice water was added, the mixture was extracted with ethyl acetate, and the organic layer was washed successively with a saturated aqueous sodium hydrogen-carbonate solution, 5% hydrochloric acid and a saturated aqueous sodium chloride solution and dried over anhydrous magnesium sulfate. After filtration, the solvent was evaporated, and the resulting crude product was washed with ethyl acetate to give 8.44 g of betamethasone 21-methoxide, which was then recrystallized from a mixture of ethyl acetate and methanol to give colorless prisms.

m.p. 228°–230° C.

(2) To a cooled (−25° C.) solution of 8.43 g of betamethasone 21-methoxide in 85 ml of pyridine was added dropwise 7.05 ml of trifluoroacetic anhydride, and after completion of the addition, the mixture was stirred at the same temperature for 30 minutes. To the reaction solution was added ice water, the mixture was extracted with ethyl acetate, and the organic layer was washed successively with 10% hydrochloric acid, a saturated aqueous sodium hydrogencarbonate solution and a saturated aqueous sodium chloride solution and dried over anhydrous magnesium sulfate. The solvent was evaporated, and the resulting crude crystals were recrystallized from a mixture of methanol and dichloromethane to give 6.66 g of betamethasone 11-trifluoroacetate 21-methoxide.

m.p. 216°–219° C. (3) To a mixture of 4.1 g of betamethasone 11-trifluoroacetate
21-methoxide obtained in the above, 15 ml of propionic acid and 15 ml of propionic anhydride was added 1 g of p-toluenesulfonic acid, and the mixture was stirred at room temperature for 4 days. After completion of the reaction, 25 ml of N,N-dimethylformamide and 20 ml of a 10% aqueous sodium acetate solution were added successively and the mixture was stirred at about 60° C for 1 hour. Then, water was added, the mixture was extracted with ethyl acetate, and the organic layer was washed successively with a saturated aqueous sodium hydrogencarbonate solution and a saturated aqueous sodium chloride solution, and dried over anhydrous magnesium sulfate. After evaporation of the solvent, the residue was applied to silica gel column chromatography (eluent; ethyl acetate : hexane=3:5) to give 2.60 g of betamethasone 17-propionate 21-methoxide (Compound 1), which was then recrystallized from ethyl acetate to give colorless prisms.

m.p. 214°–216° C.

EXAMPLE 2 [ANOTHER METHOD OF EXAMPLE 1 (2)]

To a cooled (−9° C.) solution of 84.30 g of betamethasone 21-methoxide, obtained in Example 1 (1), in 850 ml of N,N-dimethylformamide was added dropwise 74 ml of trifluoroacetic anhydride for a 30 minutes period. After the addition, the mixture was stirred at −5° C. for 30 minutes, the reaction solution was poured into water, and the precipitate was collected by filtration and washed with water, dried and washed with ethyl acetate to give 97.9 g of betamethasone 11-trifluoroacetate 21-methoxide.

EXAMPLE 3 [Another method 1 OF EXAMPLE 1 (3)]

To 134 ml of trifluoroacetic anhydride was dropwise 70.5 ml of propionic acid under ice cooling, and the mixture was stirred at room temperature for 15 minutes. 95.0 g of betamethasone 11-trifluoroacetate 21-methoxide obtained in Example 1 (2) or Example 2 was added gradually, and the mixture was stirred for a further 4 hours. After completion of the reaction, 475 ml of N,N-dimethylformamide, 258 ml of water and 186 g of sodium acetate were added under ice cooling successively and the mixture was stirred at room temperature for 30 minutes. To the reaction solution was added ethyl acetate, and the mixture was washed successively with a saturated aqueous sodium chloride solution, a saturated aqueous sodium hydrogencarbonate solution, water and a saturated aqueous sodium chloride solution and dried over anhydrous magnesium sulfate. After evaporation of the solvent, the residue was applied to silica gel column chromatography (eluent; acetone : chloroform : hexane=1:3:5) followed by recrystallization from a 95% aqueous ethanol to give 45.3 g of betamethasone 17-propionate 21-methoxide, which was identical to that obtained in Example 1 (3).

EXAMPLE 4 [ANOTHER METHOD 2 OF EXAMPLE 1 (3)]

To a solution of 2.0 g of betamethasone 11-trifluoroacetate 21-methoxide, obtained in Example 1 (2) or Example 2, in 10 ml of dichloromethane were added 2 ml of propionic anhydride and then 0.1 ml of 70% perchloric acid, and the mixture was stirred at room temperature for 80 minutes. After completion of the reaction, 10 ml of N,N-dimethylformamide and 10 ml of an aqueous sodium acetate solution were added to the reaction solution, and the mixture was stirred at about 60° C. for 1 hour. Then, water was added, the mixture was extracted with ethyl acetate, and the organic layer was washed successively with a saturated aqueous sodium hydrogencarbonate solution and a saturated aqueous sodium chloride solution, and dried over anhydrous magnesium sulfate. After evaporation of the solvent, the residue was recrystallized from a 95% aqueous ethanol to give 1.33 g of betamethasone 17-propionate 21-methoxide, which was identical to that obtained in Example 1 (3).

Following a procedure similar to that of the above Example, there were obtained the following compounds Betamethasone 17-acetate 21-methoxide (Compound 2)
m.p. 257°–261° C.
Betamethasone 17-butyrate 21-methoxide (Compound 3)
m.p. 150°–151° C.
Betamethasone 17-isobutyrate 21-methoxide (Compound 4)
m.p. 127°–130° C.
Betamethasone 17-valerate 21-methoxide Compound 5)
m.p. 101°–103° C.
Betamethasone 17-isovalerate 21-methoxide (Compound 6)
m.p. 106°–108° C.
Betamethasone 17-acetate 21-ethoxide (Compound 7)
m.p. 250°–252° C. (dec.)
Betamethasone 17-propionate 21-ethoxide (Compound 8)
m.p. 208°–211° C.
Betamethasone 17-butyrate 21-ethoxide (Compound 9)
m.p. 106°–109° C.
Betamethasone 17-acetate 21-propoxide (Compound 10)
m.p. 228°–230° C.
Betamethasone 17-propionate 21-propoxide (Compound 11)
m.p. 203°–205° C.
Betamethasone 17-butyrate 21-propoxide (Compound 12)
m.p. 168°–169° C.
Dexamethasone 17-acetate 21-methoxide (Compound 13)
m.p. 242°–245° C.
Dexamethasone 17-propionate 21-methoxide (Compound 14)
m.p. 216°–217° C.
Dexamethasone 17-butyrate 21-methoxide (Compound 15)
m.p. 172°–173° C.
Dexamethasone 17-acetate 21-ethoxide (Compound 16)
m.p. 211°–213° C.
Dexamethasone 17-propionate 21-ethoxide (Compound 17)
m.p. 194°–195° C.
Dexamethasone 17-butyrate 21-ethoxide (Compound 18)
m.p. 189°–190° C.
Dexamethasone 17-propionate 21-propoxide (Compound 19)
m.p. 165°–167° C.

EXAMPLE 5

To a solution of 1.00 g of betamethasone 17-propionate in 50 ml of acetonitrile were added 4.21 ml of acetic anhydride, 3.16 ml of dimethyl sulfoxide and 1.27 ml of acetic acid, and then the mixture was refluxed for 4 hours. After evaporation of the solvent, the residue was poured into a 10% aqueous sodium hydrogencarbonate solution, the precipitate which separated was collected by filtration, and applied to silica gel column chromatography (eluent; acetone : chloroform : hexane=3:3:16) to give 280 mg of betamethasone 17-propionate 21-methylthiomethyleneoxide (Compound 20).
m.p. 215–218° C.

What is claimed is:

1. A 21-alkoxysteroid compound represented by the formula

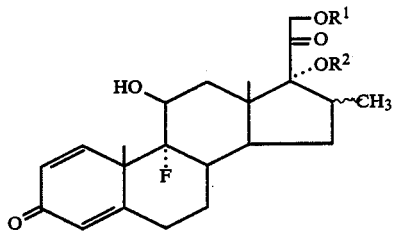

wherein $R^1$ is an alkyl group having 1 to 4 carbon atoms or a methylthiomethyl group, $R^2$ is an alkanoyl group having 2 to 7 carbon atoms, and a wavy line indicates the α- or β-configuration.

2. A 21-alkoxysteroid compound according to claim 1, wherein the alkyl group of $R^1$ is a methyl group, an ethyl group or a propyl group.

3. A 21-alkoxysteroid compound according to claim 1, wherein the alkanoyl group of $R^2$ is an acetyl group, a propionyl group, a butyryl group, an isobutyryl group, a valeryl group or an isovarleryl group.

* * * * *

UNITED STATES PATENT AND TRADEMARK OFFICE
CERTIFICATE OF CORRECTION

PATENT NO. : 4,968,822
DATED : November 6, 1990
INVENTOR(S) : MITSUKUCHI et al

It is certified that error appears in the above-identified patent and that said Letters Patent is hereby corrected as shown below:

Col. 1, line 16, "allegic" should read --allergic--; and line 24, "successed" should read --succeeded--.

Col. 2, line 51, "R3-X" should read --$R^3$-X--.

Col. 3, line 41, "t 3" should read --to 3--.

Col. 4, line 45, "calcurated" should read --calculated--.

Col. 5, line 8, delete "as", first instance; and line 62, after "C." begin a new paragraph.

UNITED STATES PATENT AND TRADEMARK OFFICE
CERTIFICATE OF CORRECTION

PATENT NO. : 4,968,822

DATED : November 6, 1990

INVENTOR(S) : Mitsukuchi et al

It is certified that error appears in the above-identified patent and that said Letters Patent is hereby corrected as shown below:

Col. 6, line 21, "minutes" should read --minute--.

Col. 7, line 19, "Compound" should read --compound--.

Col. 8, line 49, "isovarleryl" should read --isovaleryl".

Signed and Sealed this

Fifth Day of May, 1992

Attest:

DOUGLAS B. COMER

Attesting Officer

Acting Commissioner of Patents and Trademarks